United States Patent [19]
Annett

[11] Patent Number: 5,162,040
[45] Date of Patent: Nov. 10, 1992

[54] MEDICAL DRESSING PACKAGE AND METHODS

[75] Inventor: Leland W. Annett, Lake Elmo, Minn.

[73] Assignee: Medical Concepts Development, Inc., St. Paul, Minn.

[21] Appl. No.: 433,567

[22] Filed: Nov. 8, 1989

[51] Int. Cl.⁵ .................. A61F 13/00; A61B 17/06; A61B 19/00

[52] U.S. Cl. ............................ 602/57; 206/441; 128/849; 128/888

[58] Field of Search ............ 128/155, 849, 888, 887; 206/440, 441; 604/307; 602/57, 42

[56] References Cited

U.S. PATENT DOCUMENTS

| | | | |
|---|---|---|---|
| 1,852,040 | 4/1932 | Blank | 604/304 |
| 2,473,062 | 6/1949 | Kennedy et al. | 604/307 |
| 4,781,293 | 11/1988 | Johns | 206/441 |
| 4,815,457 | 3/1989 | Mazars et al. | 128/155 |
| 4,837,062 | 6/1989 | Dunshee et al. | 128/155 |
| 4,926,850 | 5/1990 | Lott et al. | 128/155 |

Primary Examiner—Paul Prebilic
Attorney, Agent, or Firm—Lawrence M. Nawrocki

[57] ABSTRACT

A sterile, medical dressing package (10), a method of applying the dressing (10) to a patient, and a method of configuring and packaging a sterile, medical dressing (10). The package (10) includes a dressing sheet (12) and a pair of cover sheets (14). Release portions (38) of the cover sheets (14) overlie, and are adhered to, lateral portions (36) of an adhesive face (16) of the dressing sheet (12). Tab portions (40) of the cover sheets (14) are folded back upon their respective release portions (38). The tab portions (40) extend away from a central portion (34) of the dressing sheet (12). The central portion (34) of the dressing sheet (12) is folded back upon, and adhered to, a tab portion (40) of one of the cover sheets (14).

5 Claims, 1 Drawing Sheet

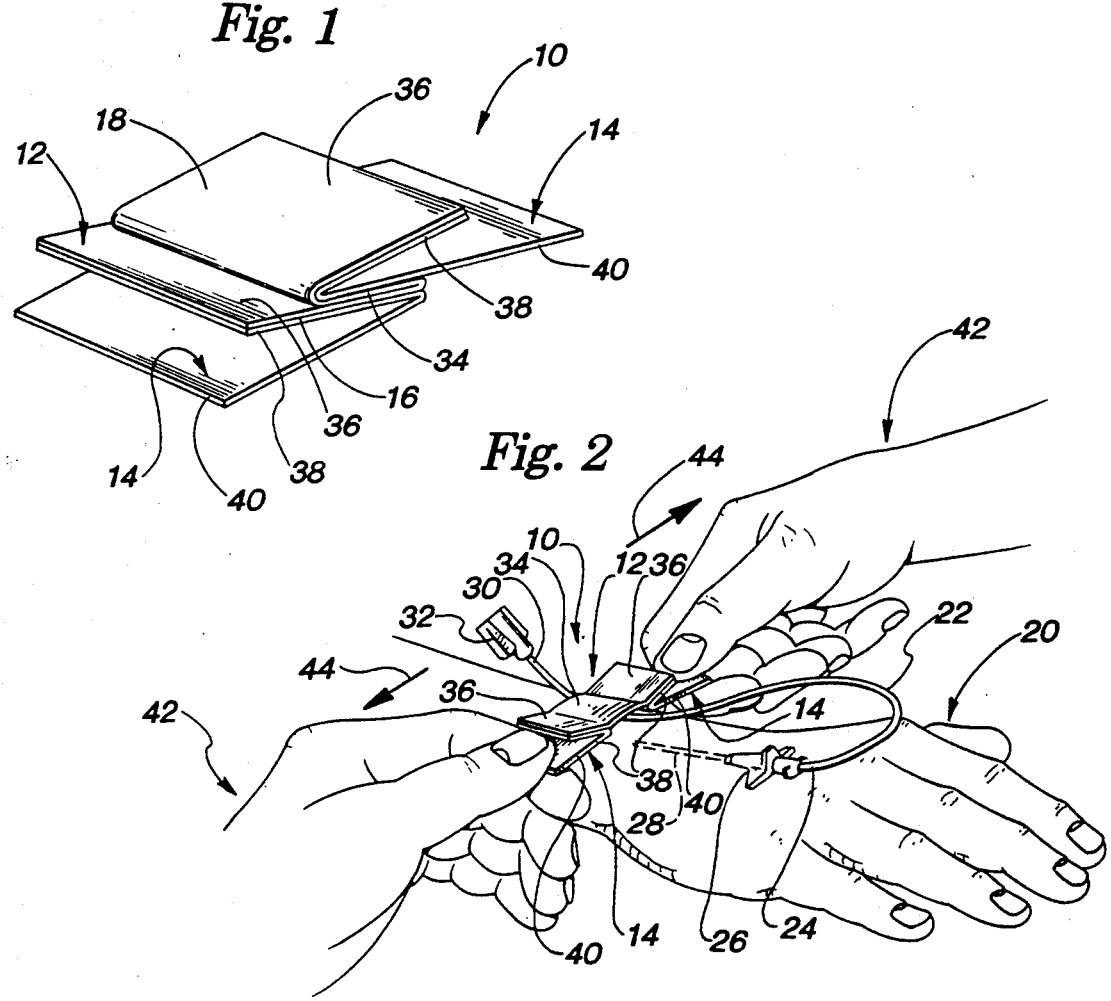
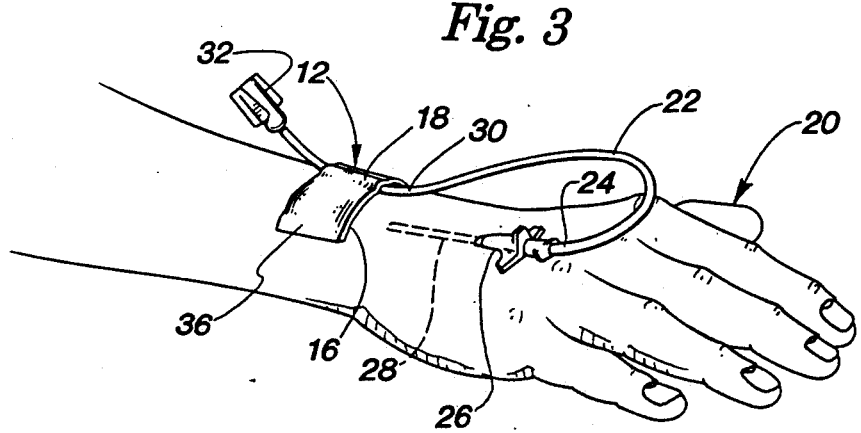

MEDICAL DRESSING PACKAGE AND METHODS

TECHNICAL FIELD

The present invention deals broadly with medical technology and structures employed therein. More narrowly, however, the invention deals with medical dressing constructions and methods for packaging and applying them to a patient.

BACKGROUND OF THE INVENTION

There are numerous problems incident to the protection of a patient being treated under emergency circumstances or by surgical procedure. Most notable of these factors include maintenance of the patient's vital signs and, often, controlling of bleeding. Both of these factors bear upon the ability of the medical personnel to maintain the patient's life.

Other less thought of considerations are also involved, however. One significant factor of this type is the maintenance of a sterile atmosphere in which the patient is treated in order to minimize the chances of infection occurring. Not only does infection have a bearing upon the long-term health and well-being of the patient, but it can cause the very loss of life.

For this reason, therefore, the cleanliness and sterility of hospital emergency rooms are sought to be maximized. This is also true with regard to hospital operating rooms. A "sterile field" is maintained in the immediate area where a surgical procedure is being performed, and intense efforts are made to maintain total sterility within the field.

All implements brought into the field are previously sterilized, and sponges, swabs, bandages, and other dressings are maintained in a sterile condition prior to, and during, the performance of the procedure. Wound dressings are packaged and maintained in a sterile state through the time that they are applied to a patient.

Conditions which are, as much as possible, sterile are sought to be achieved in other environments also. As previously discussed, emergency rooms are a location where sterility is important. Anywhere an adhesive applied applique is brought into contact with a puncture or wound in a patient's skin, sterility is of concern in order to minimize the chances of infection. Another such instance is the application of an IV cover. Typically, such an adhesive applied cover is brought into contact with, for example, the dorsal side of a patient's hand in order to maintain and cover the entry point of the IV needle. More commonly, the cover is placed directly over the point at which the needle enters the skin overlying the vein entered. In other applications, however, the cover can be employed to reduce tension in the IV feed tube. In this application, the adhesive applied dressing might be spaced at some distance from the actual point of entry of the needle. In any case, however, sterility is a concern.

Another consideration that must be taken into account during setting up of IV's, emergency treatment, performance of surgical procedures, etc. is the ease of application and securing of medical dressings and IV covers. The functions with which the medical personnel are tasked sometimes make it difficult to manipulate dressings and IV covers. The easier manipulation is made, the smoother the task can be accomplished.

Another desirable feature of a medical dressing or IV cover, above and beyond those dictated by the factors discussed above, is compactness in packaging. This factor bears upon the size of the storage area which must be made available, and the accessibility of the package when performing a task requiring a dressing or IV cover.

It is to these problems and dictates of the prior art that the present invention is directed. It is an improved medical dressing device, a method of applying the device, and a method of packaging a sterile medical dressing. Because of the nature of the invention, various problems of the prior art are solved.

SUMMARY OF THE INVENTION

The present invention includes a medical dressing device, a method of configuring and packaging the device, and a method of applying the device. The device includes a flexible dressing sheet, the sheet having adhesive and non-adhesive sides. The adhesive side has a central portion, intermediate opposite ends of the sheet, to be applied to a site on a patient, for example, to cover an IV needle insertion. The adhesive side of the dressing sheet also includes a pair of lateral portions, one on either side of the central portion. Each of a pair of cover sheets includes a release portion, and the release portion of each of the cover sheets overlies, and is adhered to, one of the lateral portions of the dressing sheet. Each cover sheet, additionally, includes a tab portion which is folded back on its corresponding release portion. The fold is such that each tab portion extends away from the central portion of the dressing sheet. The central portion of the adhesive side of the dressing sheet is, in turn, folded back on, and adhered to, the tab portion of one of the cover sheets. The adhesive surface of the central portion of the dressing sheet is, thereby, covered.

Typically, the shape of the sterile medical dressing package in accordance with the present invention is that of a dressing known in the prior art. That is, the shape can be rectangular.

The invention also encompasses a method of applying such a sterile medical dressing package to a site on a patient. The method of application includes a step of grasping the tab portion of each cover sheet. The tab portions are, thereafter, drawn away from one another to release the central portion of the adhesive side of the dressing sheet from its disposition adhered to the tab portion of the cover sheet on which it has been folded back. The adhesive surface of the central portion of the dressing sheet, thereby, becomes exposed. That adhesive surface is then applied to the desired site on the patient.

Thereafter, the tab portions continue to be withdrawn from the lateral portions of the dressing sheet by drawing them in the same directions they were drawn to expose the central portion of the dressing sheet. The lateral portions of the dressing sheet, thereby, become exposed. Pressure can then be applied to the non-adhesive side of the dressing sheet to securely adhere the dressing sheet at the desired site.

The invention also includes a method of configuring and packaging a sterile medical dressing. The configuring and packaging method includes a first step of providing a flexible dressing sheet which includes an adhesive side having a central portion to be applied at a site on a patient. The adhesive side of the dressing sheet also includes a pair of lateral portions, one on either side of the central portion.

A cover sheet is applied to each of the lateral portions of the dressing sheet with a release portion of each cover sheet overlying, and being adhered to, a corresponding lateral portion of the dressing sheet. With this disposition of the cover sheets, a tab portion of each cover sheet is folded back upon its corresponding release portion in a direction away from the central portion of the dressing sheet. A central portion of the dressing sheet is, thereafter, folded back on, and adhered to, the tab portion of one of the cover sheets.

The present invention is thus an improved sterile, medical dressing package, a method of applying the sterile, medical dressing package to a site on a patient, and a method of configuring and packaging a medical dressing. More specific features and advantages obtained in view of those features will become apparent with reference to the DETAILED DESCRIPTION OF THE INVENTION, appended claims, and accompanying drawing figures.

BRIEF DESCRIPTION OF THE DRAWING

FIG. 1 is a perspective view of a medical dressing package in accordance with the present invention;

FIG. 2 is a perspective view of the package being deployed to effect strain relief of an IV tube; and FIG. 3 is a perspective view after the dressing application has been completed.

DETAILED DESCRIPTION OF THE INVENTION

Referring now to the drawing figures wherein like reference numerals denote like elements through the several views, FIG. 1 shows a sterile medical dressing package 10 in accordance with the present invention. The package 10 includes a dressing sheet 12 which is actually applied to a site on a patient, as seen in FIGS. 2 and 3. Additionally, the package 10 includes a pair of cover sheets 14 which cover and maintain sterile an adhesive side 16 of the dressing sheet 12.

The dressing sheet 12 has adhesive and non-adhesive faces 16, 18. FIGS. 2 and 3 illustrate, by way of example, the hand 20 of a patient to which an IV is being applied. A pig-tail type tube 22 has, at a first end 24, a fitting 26 mounting the IV needle 28. The other end 30 of the tube 22 is provided with a second fitting 32 which is mated to the IV system (not shown).

The figures show the needle 28 mounted to the fitting 26 at the first end 24 of the pig-tail type tube 22 already inserted in a vein in the patient's hand 20. The package in accordance with the present invention, in the application of FIGS. 2 and 3, is being applied to effect strain relief so that the needle 28 will not be withdrawn from the hand 20 of the patient.

To this end, the adhesive side 16 of the dressing sheet 12 is engaged with, and securely adhered to, a site on the patient's hand 20 with the tube 22 affixed under the dressing sheet 12 at the desired site. FIG. 2 shows the process of affixation, and FIG. 3 shows the disposition after affixation has been completed.

Referring again to FIG. 1, the dressing sheet 12 is divided into a central portion 34, which, after application, overlies the actual location at the site. The dressing sheet 12 also includes lateral portions 36, one on either side of the central portion 34. It will be understood, however, that the dressing sheet 12 is, in fact, one continuous sheet which need not have any lines of demarcation delineating between the central portion 34 and lateral portions 36. It will also be understood, in view of this disclosure, that the full adhesive side or face 16 of the dressing sheet 12 is tacky. That is, the adhesive side 16 encompassing both the central portion 34 and the lateral portions 36 has adhesive applied thereto.

Each cover sheet 14 comprises a release portion 38 and a tab portion 40. The release portion 38 of each cover sheet 14 overlies, and is adhered to, a corresponding lateral portion 36 of the dressing sheet 12. The tab portion 40 of each cover sheet 14 is folded back on its corresponding release portion 38 and extends away from the central portion 34 of the dressing sheet 12.

As will be able to be seen then, in view of this disclosure, the medical dressing package 10 can be disposed in a configuration as seen in FIG. 2 with the adhesive face 16 of the central portion 34 of the dressing sheet 12 exposed for application of the dressing 10 to a patient. FIG. 1, however, illustrates a configuration of the dressing 10 constructed so that the adhesive surface 16 of the dressing sheet 12 is maintained covered and tackiness of that surface 16 is not lost. The tab portions 40 of the cover sheets 14 are provided with a longitudinal dimension sufficient so that the central portion 34 of the adhesive side 16 of the dressing sheet 12 can be folded back on, and adhered to, either of those tab portions 40.

In the prior art, dressings of a nature similar to that of the present invention are rectangular in shape. While not exclusively contemplated within the bounds of the present invention, a rectangular configuration is shown in the figures. A package 10 so shaped and folded as described above can be made compact and, therefore, be rendered better able to be wrapped for shipment and storage. Additionally, because of the compactness, the wrapped package 10 can be more accessible, for example, during the performance of a surgical procedure.

While not shown in the drawing figures, It will be understood that, when the package 10 is made available commercially, it would likely be wrapped in an appropriate manner. Typically, a sterile paper would be used for this purpose.

FIG. 1 illustrates the package 10 after the wrapping is removed. In order to apply the dressing 10 to a patient, a medical person making the application would grab the tab portions 40 of the cover sheets 14 with his or her hands 42, as shown in FIG. 2. As the tab portions 40 are drawn outwardly away from the central portion 34 of the dressing sheet 12 in the direction of the arrows 44 in FIG. 2, the central portion 34 of the dressing sheet 12 will, initially, become exposed as a result of it becoming unfolded away from the tab portion 40 upon which it was previously folded and adhered.

With the central portion 34 of the dressing sheet 12 thus exposed, the adhesive face 16 of the central portion 34 can be engaged with the patient's hand 20, over the IV tube 22, and adhered, in some measure, to the patient's hand 20. The application of additional pressure to the cover sheets 14 to draw the tabs 40 in a direction away from the central portion 34 of the dressing sheet 12 will serve to draw the release portions 38 of the cover sheets 14 away from the lateral portions 36 of the dressing sheet 12. The adhesive faces of the lateral portions 36 of the dressing sheet 12 will, thereby, become exposed also. The cover sheets 14 can then be discarded.

At this point during application of the dressing 10, the medical person who has performed the task can securely adhere the dressing 10 to the patient. This is accomplished by applying downward pressure to enable the full adhesive surface 16 of the dressing sheet 12 to tightly engage the patient's skin.

Numerous characteristics and advantages of the invention have been set forth in the foregoing description. It will be understood, of course, that this disclosure is, in many respects, only illustrative. Changes can be made in details, particularly in matters of shape, size, and arrangement of parts without exceeding the scope of the invention. The invention's scope is defined in the language in which the appended claims are expressed.

What is claimed is:

1. A sterile, medical dressing package, comprising:
    (a) a felxible dressing sheet with opposite ends, said sheet having an adhesive side with a central portion to be applied at a site on a patient and a pair of lateral portions, one on either side of said central portion; and
    (b) a pair of cover sheets, each having a release portion overlying one of said lateral portions of said dressing sheet, and a tab portion folded back on a corresponding release portion away from said central portion of said dressing sheet, at least one of said tab portions having a length greater than a longitudinal dimension of said central portion of said flexible dressing sheet;
    (c) said central portion of said adhesive side of said dressing sheet being folded back on, and adhered to, one of said tab portions which has a length greater than a longitudinal dimension of said central portion of said flexible dressing sheet, and leaving both of said tab portions accessible.

2. A package in accordance with claim 1 wherein said dressing sheet is generally rectangular in shape.

3. A method of applying a sterile medical dressing package in accordance with claim 1, comprising the steps of:
    (a) grasping the tab portion of each cover sheet;
    (b) drawing the tab portions away from one another to release the central portion of the adhesive side of the dressing sheet from the tab portion of the cover sheet on which it has been folded back and to which it has been adhered, in order to expose the central portion of the adhesive side of the dressing sheet;
    (c) applying the central portion of the adhesive side of the dressing sheet directly to a desired site; and
    (d) continuing to withdraw the tab portions from the lateral portions of the dressing sheet.

4. A method in accordance with claim 3, comprising the further step of:
    (e) applying pressure to a non-adhesive side of the dressing sheet to securely adhere the dressing sheet at the site.

5. A method of configuring and packaging a sterile, medical dressing, comprising the steps of:
    (a) providing a flexible dressing sheet having an adhesive side with a central portion to be applied at a site on a patient, and a pair of lateral portions, one on either side of said central portion;
    (b) applying a cover sheet to each of the lateral portions of the dressing sheet with a release portion of each cover sheet overlying, and adhered to, the corresponding lateral portion of the dressing sheet, and with a tab portion of each cover sheet, at least one of which tab portions has a length greater than a longitudinal dimension of the central portion of the flexible dressing sheet folded back upon its corresponding release portion away from the central portion of the dressing sheet;
    (c) folding the central portion of the dressing sheet back on, and adhered to, one of said tab portions which has a length greater than a longitudinal dimension of the central portion of the flexible dressing sheet; and
    (d) leaving both of the tab portions accessible.

* * * * *